United States Patent
Lee et al.

(10) Patent No.: US 9,901,735 B1
(45) Date of Patent: Feb. 27, 2018

(54) ANCILLARY DEVICE FOR ELECTRICAL STIMULATION DEVICE AND ELECTRICAL STIMULATION DEVICE

(71) Applicant: y-Brain Inc, Daejeon (KR)

(72) Inventors: Ki Won Lee, Seongnam-si (KR); Cheon Ju Ko, Yongin-si (KR); Jong Min Jang, Suwon-si (KR); Byung Gik Kim, Daegu (KR)

(73) Assignee: y-Brain Inc, Daejeon (KR)

( * ) Notice: Subject to any disclaimer, the term of this patent is extended or adjusted under 35 U.S.C. 154(b) by 83 days.

(21) Appl. No.: 15/229,077

(22) Filed: Aug. 4, 2016

(51) Int. Cl.
*A61N 1/08* (2006.01)
*A61N 1/36* (2006.01)
*A61N 1/20* (2006.01)
*A61N 1/04* (2006.01)

(52) U.S. Cl.
CPC ....... *A61N 1/36025* (2013.01); *A61N 1/0484* (2013.01); *A61N 1/0492* (2013.01); *A61N 1/205* (2013.01)

(58) Field of Classification Search
CPC ...... A61N 1/0404–1/0456; A61N 1/08; A61N 1/3603; A61N 1/36031; A61N 1/36014
See application file for complete search history.

(56) References Cited

U.S. PATENT DOCUMENTS

| | | | |
|---|---|---|---|
| 4,926,879 A * | 5/1990 | Sevrain | A61F 11/04 340/407.1 |
| 6,059,736 A * | 5/2000 | Tapper | A61N 1/0436 600/573 |
| 6,575,957 B1 * | 6/2003 | Tapper | A61N 1/044 604/20 |
| 6,678,554 B1 * | 1/2004 | Sun | A61N 1/044 604/20 |
| 2002/0173743 A1 * | 11/2002 | Tapper | A61N 1/044 604/20 |
| 2003/0055460 A1 * | 3/2003 | Owen | A61N 1/0452 607/5 |
| 2004/0193222 A1 * | 9/2004 | Sullivan | A61N 1/3625 607/9 |
| 2009/0216175 A1 * | 8/2009 | Matsumura | A61N 1/0428 604/20 |

(Continued)

FOREIGN PATENT DOCUMENTS

| | | |
|---|---|---|
| JP | 10-508526 A | 8/1998 |
| JP | 2009-530064 A | 8/2009 |
| KR | 10-2010-0040683 A | 4/2010 |

OTHER PUBLICATIONS

Korean Office Action for corresponding Korean Patent Application No. 10-2015-0054430 dated Jul. 29, 2015.

(Continued)

*Primary Examiner* — Kennedy Schaetzle
(74) *Attorney, Agent, or Firm* — Hauptman Ham, LLP

(57) ABSTRACT

Provided are an ancillary device for an electrical stimulation device and an electrical stimulation device. The ancillary device is usable for an electrical stimulation device including at least one electrode that contacts the head of a user to apply a current to the head of a user, and includes a reverse current supplier that contacts the at least one electrode of the electrical stimulation device, and a controller that controls the reverse current supplier such that a reverse current is supplied to the at least one electrode to neutralize the at least one electrode.

8 Claims, 9 Drawing Sheets

(56) References Cited

U.S. PATENT DOCUMENTS

| | | | | |
|---|---|---|---|---|
| 2012/0330384 A1* | 12/2012 | Perryman | .......... | A61N 1/36125 |
| | | | | 607/72 |
| 2013/0023953 A1* | 1/2013 | van den Honert | ... | A61N 1/0541 |
| | | | | 607/56 |
| 2015/0335876 A1* | 11/2015 | Jeffery | ................ | A61N 1/0456 |
| | | | | 607/139 |
| 2015/0343208 A1* | 12/2015 | Davidovitch | ............ | A61C 7/00 |
| | | | | 433/6 |
| 2016/0296269 A1* | 10/2016 | Rubinsky | .................. | C25B 1/26 |

OTHER PUBLICATIONS

Korean Office Action for corresponding Korean Patent Application No. 10-2015-0054430 dated Oct. 29, 2015.

* cited by examiner

ANCILLARY DEVICE FOR ELECTRICAL STIMULATION DEVICE AND ELECTRICAL STIMULATION DEVICE

BACKGROUND

The inventive concept relates to an ancillary device for an electrical stimulation device and an electrical stimulation device.

Meanwhile, a brain electrical stimulation technology using a transcranial direct current stimulation (tDCS) is known to be effective to improve a recognition ability and treat mental diseases such as depression or attention deficit hyperactivity disorders (ADHD).

Accordingly, if the bran electrical stimulation technology may be used in everyday lives, the brain function may be improved, and mental diseases may be continuously treated by activating or retraining connections between nerves.

A tDCS device according to the related art includes a plurality of electrodes, and each of the electrodes includes a patch layer that contacts skin of the head of the user and an electrode layer that transfers a current to the patch layer. The patch layer contains an electrolyte for flows of currents, and thus an oxidation/reduction reaction may occur on an interface between the patch layer and the electrode layer. The oxidation/reduction reaction gradually acidifies or basifies the patch layer, and if the pH index of the patch layer deviates from a threshold range, the skin of the head of the user, which contacts the patch layer, may be burned.

SUMMARY

Accordingly, the inventive concept has been made in an effort to solve the above-mentioned problems, and provides an ancillary device for an electrical stimulation device and an electrical stimulation device that may prevent skin of the head of the user from being burned when the user uses the electrical stimulation device.

In accordance with an aspect of the inventive concept, there is provided an ancillary device for an electrical stimulation device including at least one electrode that contacts the head of a user to apply a current to the head of a user, the ancillary device being able to be applied to the electrical stimulation device, the ancillary device including a reverse current supplier that contacts the at least one electrode of the electrical stimulation device, and a controller that controls the reverse current supplier such that a reverse current is supplied to the at least one electrode to neutralize the at least one electrode.

In some embodiments, the ancillary device may further include a pH measurer that measures a pH index of the at least one electrode, and the controller may control the reverse current supplier such that the reverse current is supplied to the at least one electrode when the pH index of the at least one electrode, which is measured by the pH measurer, exceeds a reference pH index range.

In some embodiments, the ancillary device may further include an electrolyte supplier that contacts the at least one electrode, and the controller may control the electrolyte supplier such that the electrolyte is supplied to the at least one electrode.

Further, the ancillary device may further include a concentration measurer that measures a concentration of an electrolyte of the at least one electrode, and the controller may control the electrolyte supplier such that the electrolyte is supplied to the at least one electrode when the concentration of the electrolyte of the at least one electrode, which is measured by the concentration measurer, is lower than a reference concentration.

In some embodiments, the ancillary device may further include an indicator that indicates an operational state of the reverse current supplier or the electrolyte supplier.

In accordance with another aspect of the inventive concept, there is provided an electrical stimulation device including at least one electrode that contacts the head of a user to apply a current to the head of the user, a reverse current supplier that contacts the at least one electrode, and a controller that controls the reverse current supplier such that a reverse current is supplied to the at least one electrode to neutralize the at least one electrode.

In some embodiments, the electrical stimulation device may further include a pH measurer that measures a pH index of the at least one electrode, and the controller may control the reverse current supplier such that the reverse current is supplied to the at least one electrode when the pH index of the at least one electrode, which is measured by the pH measurer, exceeds a reference pH index range.

In some embodiments, the electrical stimulation device may further include an electrolyte supplier that contacts the at least one electrode, and the controller may control the electrolyte supplier such that the electrolyte is supplied to the at least one electrode.

Further, the electrical stimulation device may further include a concentration measurer that measures a concentration of an electrolyte of the at least one electrode, and the controller may control the electrolyte supplier such that the electrolyte is supplied to the at least one electrode when the concentration of the electrolyte of the at least one electrode, which is measured by the concentration measurer, is lower than a reference concentration.

In some embodiments, the electrical stimulation device may further include an indicator that indicates an operational state of the reverse current supplier or the electrolyte supplier.

BRIEF DESCRIPTION OF THE FIGURES

The above and other objects and features will become apparent from the following description with reference to the following figures, wherein like reference numerals refer to like parts throughout the various figures unless otherwise specified, and wherein.

DETAILED DESCRIPTION

Figure 1:
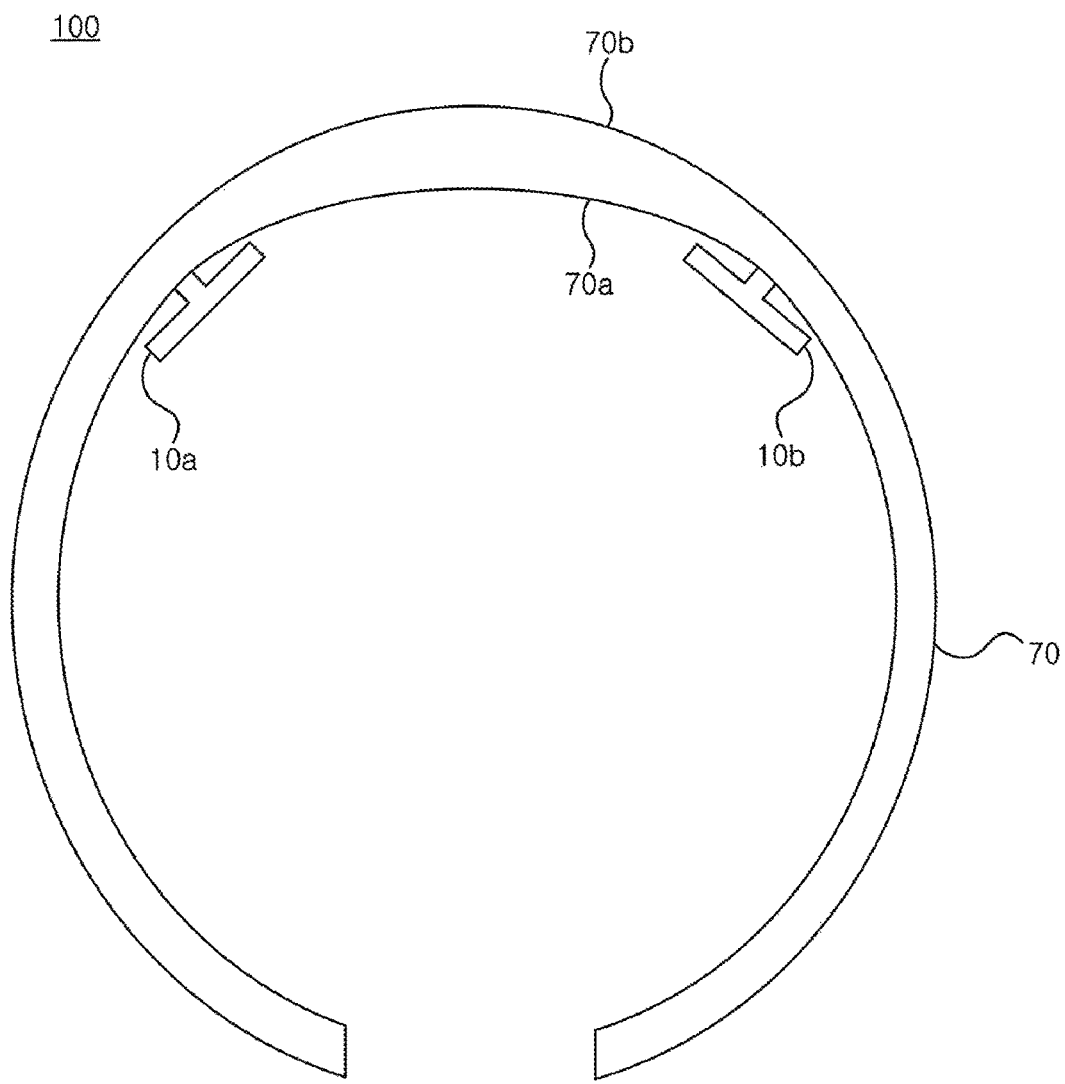
FIG. 1 is a block diagram illustrating a schematic external appearance of an electrical stimulation device, to which an ancillary device may be applied, according to an embodiment of the inventive concept.

Hereinafter, exemplary embodiments of the inventive concept will be described in detail with reference to the accompanying drawings. The above and other aspects, features and advantages of the invention will become apparent from the following description of the following embodiments given in conjunction with the accompanying drawings. However, the inventive concept is not limited to the embodiments disclosed below, but may be implemented in various forms. The embodiments of the inventive concept is provided to make the disclosure of the inventive concept complete and fully inform those skilled in the art to which the inventive concept pertains of the scope of the inventive concept. The same reference numerals denote the same elements throughout the specification.

Unless otherwise defined, all terms (including technical and scientific terms) used herein have the same meaning as commonly understood by those skilled in the art to which the inventive concept pertains. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein.

The terms used herein are provided to describe the embodiments but not to limit the inventive concept. In the specification, the singular forms include plural forms unless particularly mentioned. The terms "comprises" and/or "comprising" used herein does not exclude presence or addition of one or more other elements, in addition to the aforementioned elements.

Hereinafter, an ancillary device for an electrical stimulation device and an electrical stimulation device according to embodiments of the inventive concept will be described with reference to the accompanying drawings.

"Electrical stimulation" that will be mentioned in the following may refer to transcranial current stimulation (tCS) such as transcranial direct current stimulation (tDCS), transcranial alternating current stimulation (tACS), and transcranial random-noise stimulation (tRNS), but the inventive concept is not limited thereto.

FIG. 1 is a block diagram illustrating a schematic external appearance of an electrical stimulation device, to which an ancillary device may be applied, according to an embodiment of the inventive concept.

Referring to FIG. 1, the electrical stimulation device 100 includes a frame 70 and an electrode unit 10.

The frame 70 has a first surface 70a and a second surface 70b. The first surface 70a may be an inner surface of the frame 70, and the second surface 70b may be an outer surface of the frame 70. When the electrical stimulation device 100 is mounted on or attached to the head of the user, the first surface 70a contacts the head of the user.

The electrode unit 10 may be arranged on the first surface 70a of the frame 70.

The electrode unit 10 contacts the head of the user (a target object) and applies a current to the head of the user. The user may mount the electrical stimulation device 100 on the head or may attach the electrical stimulation device 100 to the head, and thus the electrode unit 10 may contact the head of the user. For example, the electrode unit 10 may contact the forehead of the user, but the inventive concept is not limited thereto.

A plurality of electrode units 10 (a first electrode 10a and a second electrode 10b) may be provided. The electrical stimulation device 100 may apply currents to a plurality of portions of the head of the user. For example, one electrode unit 10 (for example, the first electrode 10a) may be situated adjacent to the left side of the head of the user to contact the left side of the head, and another electrode 10 (the second electrode 10b) may be situated adjacent to the right side of the head of the user to contact the right side of the head. A plurality of electrode units 10 may be controlled independently.

The electrode units 10 have polarities as described below. The electrode units 10 may be controlled to have different polarities. However, the inventive concept is not limited thereto, but some electrode units 10 may have the same polarity depending on the number of the electrode units 10.

Each of the plurality of electrode units 10 may include a patch layer 12 and an electrode layer 11.

The patch layer 12 is a layer that directly contacts skin of the head of the user. The patch layer 12 may include a single layer. The patch layer 12 applies a current transferred from the electrode layer 11 to the head of the user. To achieve this, the patch layer 12 may include an electrolyte for transferring a current. For example, the patch layer 12 may include sponge or hydrogel that contains an electrolyte, but the inventive concept is not limited thereto. The electrolyte may include chlorine ions (Cl−) that are commonly present in skin of the user. The patch layer 12 may be formed of a material having a relatively high impedance.

The electrode layer 11 is formed on the patch layer 12. The electrode layer 11 does not contact skin of the head of the user. As described above, the electrode layer 11 transfers a current to the patch layer 12 to apply an electrical stimulus to the user through the patch layer 12. For example, the electrode layer 11 may include a conductive carbon sheet or conductive silicon, but the inventive concept is not limited thereto.

Figure 2:
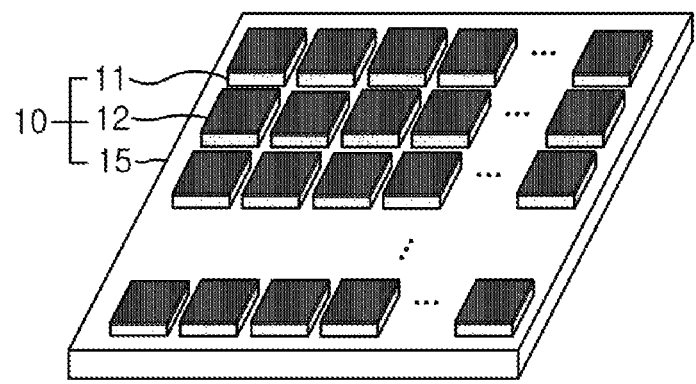
FIG. 2 is a view illustrating a configuration of an electrode unit.

As illustrated in FIG. 2, the electrode unit 10 may include a plurality of segments, and the plurality of segments may be formed on the circuit board 15 to be spaced apart from each other. Each of the segments may include a patch layer 12 and an electrode layer 11. The number, shapes, intervals of the segments may be variously modified according to embodiments. The plurality of segments may be controlled independently. Further, several segments may constitute a group to be controlled. As illustrated in FIG. 2, the electrode unit 10 may not be divided into a plurality of segments.

Although not clearly illustrated in FIG. 1, an indicator may be additionally arranged on the second surface 70b of the frame 70.

The indicator indicates polarity states of the plurality of electrode units 10. Here, "indication" may include a series of operations of directly clarifying or expressing or indirectly hinting polarity states of the plurality of electrode units 10, or sending signals such that the user may recognize the polarity states of the plurality of electrode units 10.

As an example, the indicator may include light emitting elements that are turned on and off or emit different light colors depending on the polarity states of the first electrode 10a and the second electrode 10b. One or a plurality of light emitting elements may be provided depending on the number of the electrode units 10.

As another example, the indicator may include a speaker that outputs a specific sound depending on the polarity states of the first electrode 10a and the second electrode 10b. The speaker may be used to output guide information related to the mounting of the electrical stimulation device 100.

As another example, the indicator may include a display that displays a letter, a number, a figure, an image, or the like depending on the polarity states of the first electrode 10a and the second electrode 10b.

The polarity states of the plurality of electrode units 10 may correspond to the mounting direction of the electrical stimulation device 100. This point may be particularly important when the shape of the electrical stimulation device 100 is (vertically or horizontally) symmetrical. According to an embodiment, there may be an occasion in which a flow of a current on the head of the user has to be fixed in a specific direction to allow the electrical stimulation device 100 to perform some functions or increase the effects of some functions. In this case, because the polarity states of the plurality of electrode units 10 are related to the flows of currents, it is necessary to guide the mounting direction of the electrical stimulation device 100 to the user by the electrical stimulation device 100. Accordingly, the user may recognize the mounting direction of the electrical stimulation device 100 from the indication of the indicator.

Meanwhile, the whole shape of the electrical stimulation device 100 is not limited to the embodiment of FIG. 1.

Figure 3:
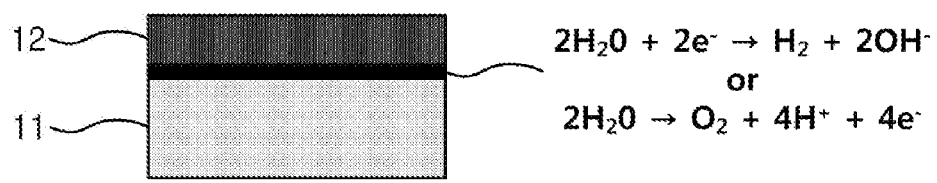
FIG. 3 is a view for explaining a water splitting reaction on an interface between a patch layer and an electrode layer.

FIG. 3 is a view for explaining a water splitting reaction on an interface between a patch layer and an electrode layer.

Referring to FIG. 3, a water splitting reaction occurs on an interface between the patch layer 12 and the electrode layer 11 when a current is transferred from the electrode layer 11 to the patch layer 12. The patch layer 12 may include water (used as a solvent) in addition to the electrolyte, and the water of the patch layer 12 reacts electrons provided by the electrode layer 11 to be split into hydroxide ions (OH+) and hydrogen molecules. Further, the water of the patch layer 12 may lose electrons to be split into hydrogen ions (H+) and oxygen molecules. Accordingly, when the electrode unit 10 functions as a cathode, the pH index of the patch layer 12 of the electrode 10 may be gradually increased by the hydroxide ions, and similarly, when the electrode unit 10 functions as an anode, the pH index of the patch layer 12 of the electrode unit 10 may be gradually decreased by the hydrogen ions. Further, the change of the pH index of the patch layer 12 deviates a threshold pH range, the skin of the head of the user, which contacts the patch layer 12 may be burned.

In order to solve this, the inventive concept discloses an ancillary device 200 for an electrical stimulation device for preventing the user from being burned by supplying a reverse current to the electrode unit 10 (the patch layer 12 of the electrode unit 10) of the electrical stimulation device 100 to neutralize the electrode unit 10.

Figure 4:
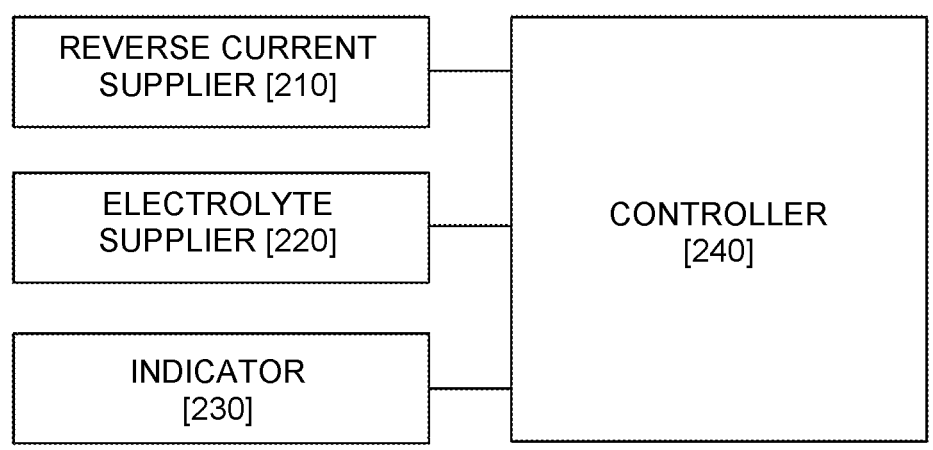
FIG. 4 is a view illustrating a schematic configuration of the ancillary device for an electrical stimulation device according to the embodiment of the inventive concept.
Figure 5:
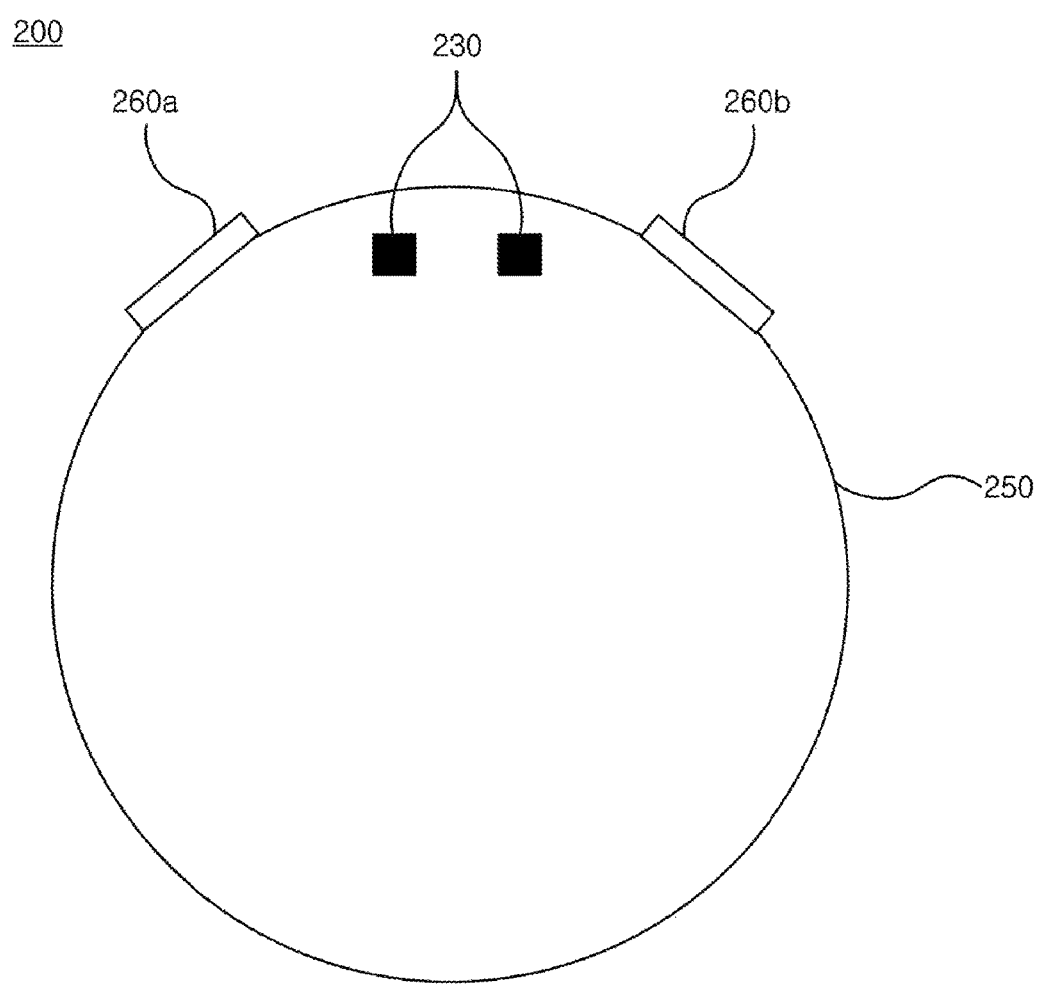
FIG. 5 is a view illustrating a schematic external appearance of the ancillary device for an electrical stimulation device according to the embodiment of the inventive concept.

FIG. 4 is a view illustrating a schematic configuration of the ancillary device for an electrical stimulation device according to the embodiment of the inventive concept. FIG. 5 is a view illustrating a schematic external appearance of the ancillary device for an electrical stimulation device according to the embodiment of the inventive concept.

Referring to FIG. 4, the ancillary device 200 for an electrical stimulation device according to an embodiment of the inventive concept includes a reverse current supplier 210, an electrolyte supplier 220, an indicator 230, and a controller 240.

The reverse current supplier 210 is configured to contact the electrodes 10a and 10b of the electrical stimulation device 100. The reverse current supplier 210 may neutralize the electrodes 10a and 10b by supplying a reverse current to the electrodes 10a and 10b of the electrical stimulation device 100. Here, "a reverse current" refers to a current having a direction that is opposite to the direction of a current on the electrodes 10a and 10b during an operation of the electrical stimulation device 100. According to an embodiment, the reverse current supplier 210 may induce a reverse current from the electrodes 10a and 10b without directly supplying a reverse current to the electrodes 10a and 10b.

The reverse current supplier 210 may transfer a reverse current to the patch layers 12 of the electrodes 10a and 10b to cause a reverse reaction of a water splitting reaction on interfaces between the patch layers 12 and the electrode layers 11 of the electrodes 10a and 10b. As the reverse reaction occurs, hydroxide ions (OH−) or hydrogen ions (H+) generated on the interfaces between the patch layers 12 and the electrode layers 11 of the electrodes 10a and 10b may be converted to water during an operation of the electrical stimulation device 100. The reverse current supplier 210 may supply a reverse current until the pH indexes of the patch layers 12 of the electrodes 10a and 10b reach a threshold pH range (that is, until the patch layers 12 of the electrodes 10a and 10b are neutralized).

The electrolyte supplier 220 is configured to contact the electrodes 10a and 10b of the electrical stimulation device 100. The electrolyte supplier 220 may supply an electrolyte to the electrodes 10a and 10b of the electrical stimulation device 100. Here, "an electrolyte" may be the same as the electrolyte contained in the patch layers 12 of the electrodes 10a and 10b. According to an embodiment, the electrolyte supplied by the electrolyte supplier 220 may contain some materials of the electrolyte 12 contained in the patch layers 12 of the electrodes 10a and 10b. A concentration of the electrolyte supplied by the electrolyte supplier 220 may be different from the concentration of the electrolyte contained in the patch layers 12 of the electrodes 10a and 10b. The electrolyte supplier 220 may additionally transfer an electrolyte (necessary) for a reverse reaction of the water splitting reaction occurring on the interfaces between the patch layers 12 and the electrode layers 11 of the electrodes 10a and 10b.

As described with reference to FIG. 3, an oxidation/reduction reaction including a water splitting reaction may occur on the interfaces between the patch layers 12 and the electrode layers 11 of the electrodes 10a and 10b. As an oxidation/reduction reaction occurs, the concentration of the electrolyte of the patch layers 12 of the electrodes 10a and 10b may be changed. Further, if the change in the concentration of the electrolyte of the patch layers 12 of the electrodes 10a and 10b deviates a threshold concentration range, a current cannot flow through the patch layers 12 so that the current transferred from the electrode layers 11 cannot be applied to the head of the user. However, according to the electrolyte supplier 220 of the inventive concept, because an electrolyte may be supplied to the patch layers 12 of the electrodes 10a and 10b, the concentration of the electrolyte of the patch layers 12 of the electrodes 10a and 10b may be maintained within the threshold concentration range. Accordingly, an effect of maintaining an electricity transfer performance of the electrode and extending the life span of the product may be obtained.

The indicator 230 indicates an operational state of the reverse current supplier 210 or the electrolyte supplier 220. Here, "indication" may include a series of operations of directly clarifying or expressing or indirectly hinting operational states of the reverse current supplier 210 or the electrolyte supplier 220, or sending signals such that the user may recognize the operational states of the reverse current supplier 210 or the electrolyte supplier 220.

For example, the indicator 230 may include a light emitting element that turns on and off light or emits different light colors depending an operational state of the reverse current supplier 210 or the electrolyte supplier 220, a speaker that outputs a predetermined sound, or a display that displays a letter, a number, a figure, an image, or the like.

The controller 240 generally controls functions and operations of the ancillary device 200 for an electrical stimulation device. The controller 240 may control the reverse current supplier 210 such that a reverse current is supplied to the electrodes 10a and 10b of the electrical stimulation device 100. The controller 240 may control the electrolyte supplier 220 such that an electrolyte is supplied to the electrodes 10a and 10b of the electrical stimulation device 100. The controller 240 may include a processor, a microprocessor, a micro controller, a central processing unit (CPU), a micro processing unit (MPU), and a micro controller unit (MCU).

Meanwhile, the elements of FIG. 4 are not essential to the ancillary device 200 for an electrical stimulation device according to the embodiment of the inventive concept, and thus the ancillary device 200 for an electrical stimulation device may include more or less elements.

Referring to FIG. 5, the ancillary device 200 for the electrical stimulation device includes a frame 250 and an electrode contact part 260.

The indicator 230 may be arranged on one surface of the frame 250. Electrode contact parts 260a and 260b that contact the electrodes 10a and 10b of the electrical stimulation device 100 may be arranged on the same or different surfaces of the frame 250.

A plurality of indicators 230 may be formed. One indicator 230 may indicate an operational state of the reverse current supplier 210, and the other indicator 230 may represent an operational state of the electrolyte supplier 220. Further, one indicator 230 may indicate a first operational state of the reverse flow supplier 210 and the electrolyte supplier 220, and the other indicator 230 may represent a second operational state. According to an embodiment, the number and the operational states of the indicators 230 may be various modified.

A plurality of electrode contact parts 260a and 260b may be formed. In some embodiments, for convenience for the user, the number of the electrode contact parts 260a and 260b may be modified to be larger than the number of the electrodes 10a and 10b of the electrical stimulation device 100. According to embodiments, the electrode contact parts 260a and 260b may protrude from the frame 250 or may be inserted into the frame 250. The sizes or areas of the electrode contact parts 260a and 260b may be larger or smaller than the sizes or areas of the electrodes 10a and 10b of the electrical stimulation device 100. The reverse current supplier 210 and the electrolyte supplier 220, which have been described above, may be arranged on the electrode contact parts 260a and 260b.

Meanwhile, the whole shape of the ancillary device 200 for an electrical stimulation device is not limited to the embodiment of FIG. 5.

Figure 6:
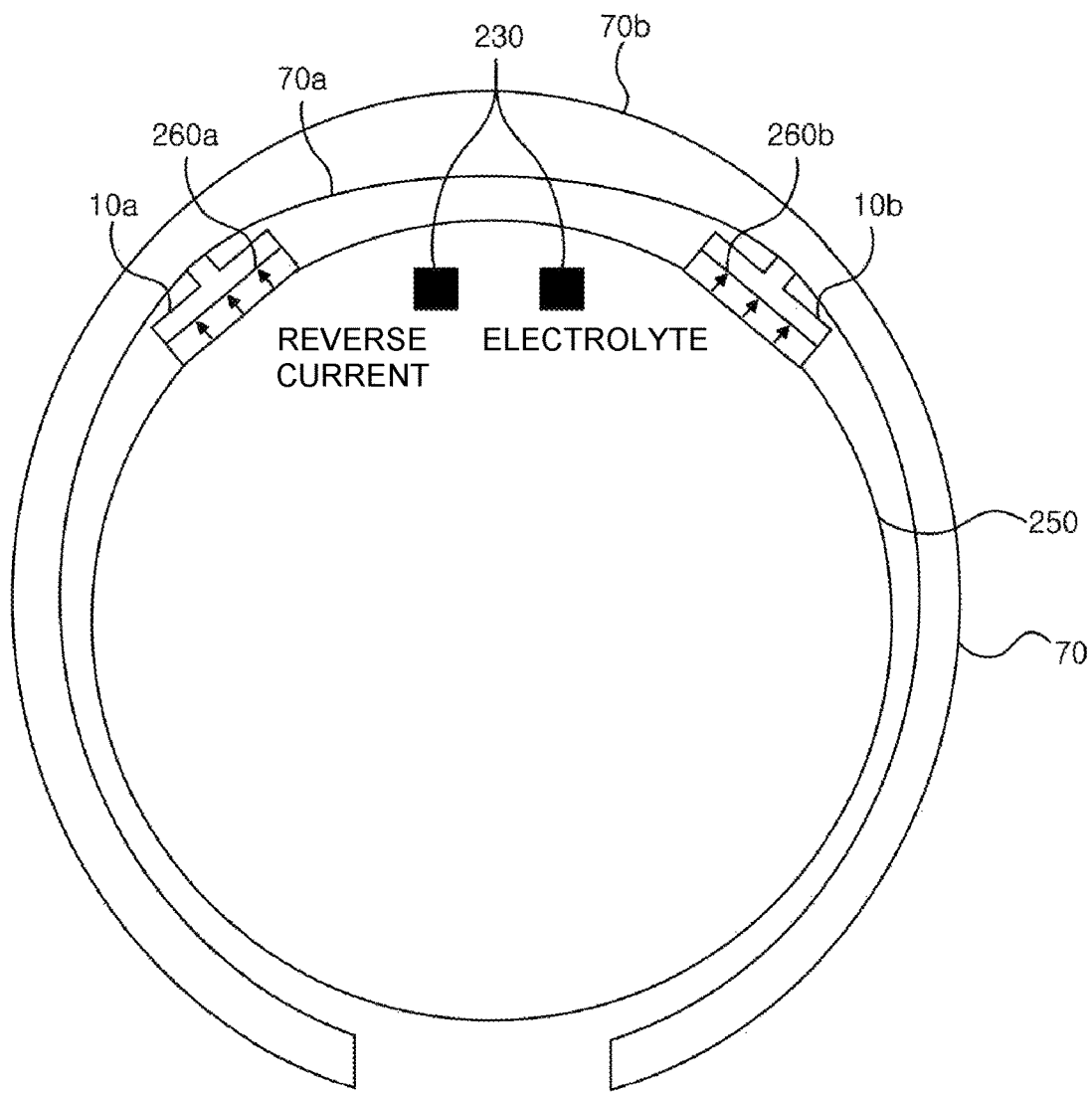
FIG. 6 is a view illustrating an operation of the ancillary device for an electrical stimulation device according to the embodiment of the inventive concept.

FIG. 6 is a view illustrating an operation of the ancillary device for an electrical stimulation device according to the embodiment of the inventive concept.

Referring to FIG. 6, in some embodiments, a reverse current supplier 210 may be arranged in a first electrode contact part 260a and an electrolyte supplier 220 may be arranged in a second electrode contact part 260b. Accordingly, a reverse current may be supplied to the first electrode 10a of the electrical stimulation device 100 and an electrolyte may be supplied to the second electrode 10b. Further, in some embodiments, the reverse current supplier 210 and the electrolyte supplier 220 may be arranged on the electrode contact parts 260a and 260b. Accordingly, a reverse current and an electrolyte may be supplied to each of the electrodes 10a and 10b of the electrical stimulation device 100. Further, the reverse current supplier 210 and/or the electrolyte supplier 220 may be arranged only in one of the first electrode contact part 260a and the second electrode contact part 260b.

According to an embodiment, the ancillary device 200 for an electrical stimulation device may function as a holder that may hold the electrical stimulation device 100.

Figure 7:
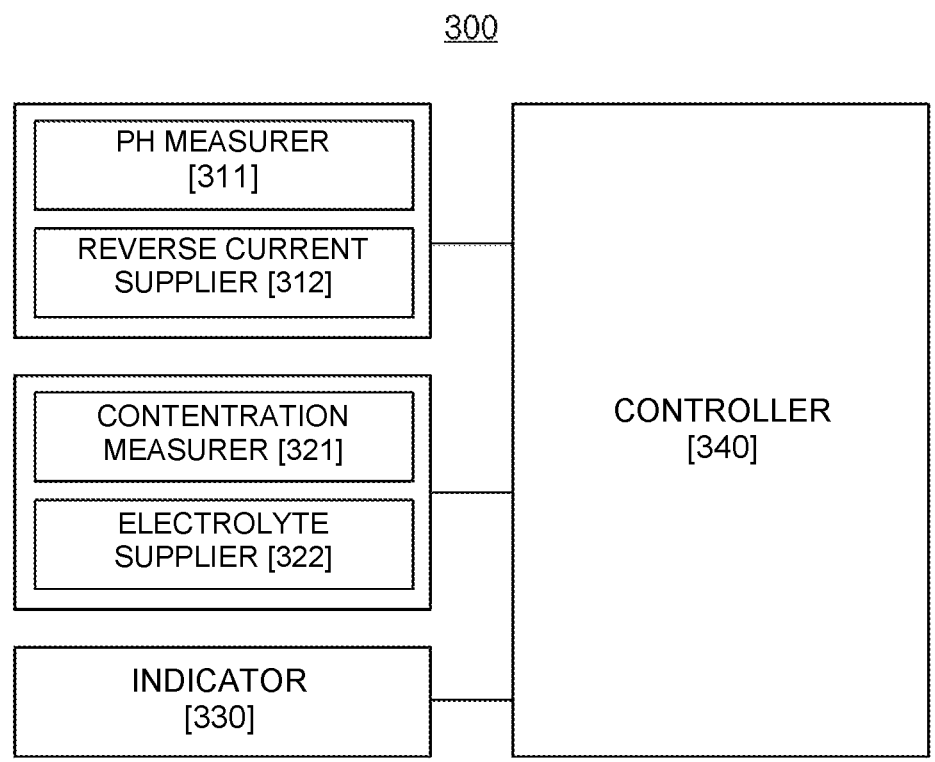
FIG. 7 is a view illustrating a schematic configuration of the ancillary device for an electrical stimulation device according to another embodiment of the inventive concept.

FIG. 7 is a view illustrating a schematic configuration of the ancillary device for an electrical stimulation device according to another embodiment of the inventive concept.

Referring to FIG. 7, the ancillary device 300 for an electrical stimulation device according to another embodiment of the inventive concept includes a pH measurer 311, a reverse current supplier 312, a concentration measurer 321, an electrolyte supplier 322, an indicator 330, and a controller 340.

The reverse current supplier 312, the electrolyte supplier 322, the indicator 330, and the controller 340 of the ancillary device 300 for an electrical stimulation device of FIG. 7 perform substantially the same operations and functions as those of the reverse current supplier 210, the electrolyte supplier 220, the indicator 230, and the controller 240 of the ancillary device 200 for an electrical stimulation device, which has been described with reference to FIG. 4.

The pH measurer 311 may measure pH indices of the electrodes 10a and 10b of the electrical stimulation device 100. The measured pH indices are transferred to the controller 340. The controller 340 may control the reverse current supplier 312 such that the reverse current supplier 312 supplies a reverse current to the electrodes 10a and 10b when the measured pH indices exceed a reference pH index range. The reference pH index range may be the same as or different from a threshold pH index range. If the pH indices of the electrodes 10a and 10b reach the reference pH index range, the reverse current supplier 312 may stop supplying the reverse current.

The concentration measurer 321 may measure concentration of the electrolyte of the electrodes 10a and 10b of the electrical stimulation device 100. The measured concentration of the electrolyte is transferred to the controller 340. The controller 340 may control the electrolyte supplier 322 such that the electrolyte supplier 322 supplies an electrolyte to the electrodes 10a and 10b when the measured concentration is lower than a reference concentration. The reference concentration may be the same as or different from a threshold concentration. If the concentration of the electrolyte of the electrodes 10a and 10b reaches the reference concentration, the electrolyte supplier 322 may stop supplying the electrolyte.

The indicator 330 may indicate information on the measured pH index and/or the measured concentration of the electrolyte.

Figure 8:
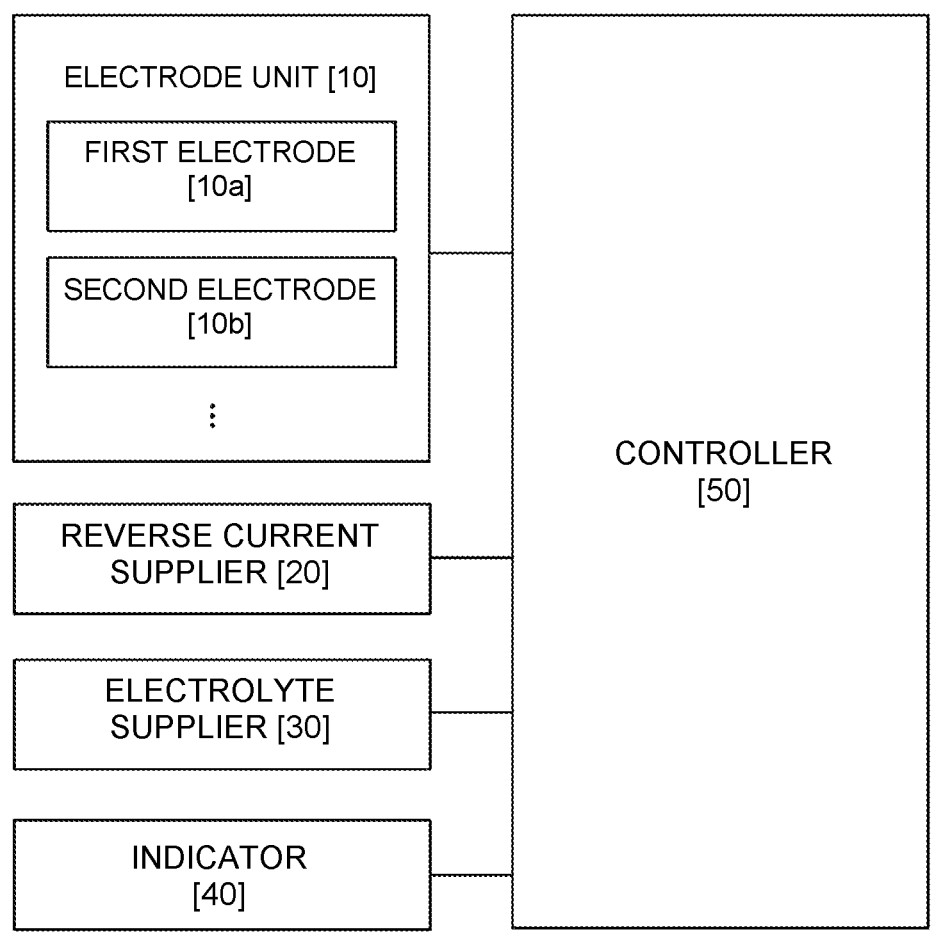
FIG. 8 is a block diagram illustrating a schematic configuration of an electrical stimulation device according to an embodiment of the inventive concept.
Figure 9:
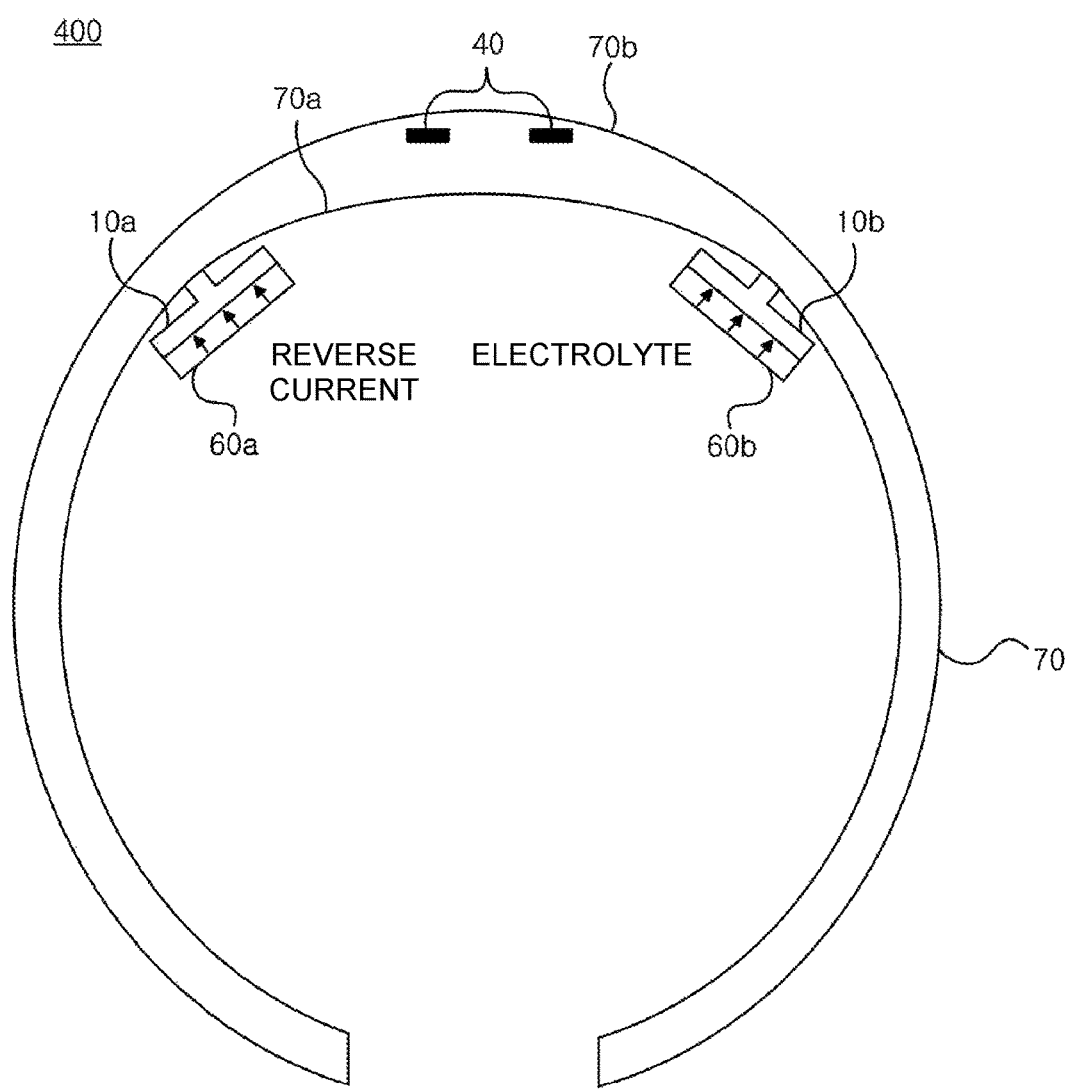
FIG. 9 is a view illustrating a schematic external appearance and an operation of the electrical stimulation device according to the embodiment of the inventive concept.

FIG. 8 is a block diagram illustrating a schematic configuration of an electrical stimulation device according to an embodiment of the inventive concept. FIG. 9 is a view illustrating a schematic external appearance and an operation of the electrical stimulation device according to the embodiment of the inventive concept.

Referring to FIGS. 8 and 9, the electrical stimulation device 400 according to an embodiment of the inventive concept includes an electrode unit 10, a reverse current supplier 20, an electrolyte supplier 30, an indicator 40, a controller 50, an electrode contact part 60, and a frame 70.

The electrical stimulation device 400 of FIGS. 8 and 9 may perform substantially the same operations and functions as those of the electrical stimulation device 100 which has been described with reference to FIG. 1. Further, the reverse current supplier 20, the electrolyte supplier 30, the indicator 40, the controller 50, and the electrode contact part 60 added to the electrical stimulation device 100 described with reference to FIG. 1 perform substantially the same operations and functions as those of the reverse current supplier 210, the electrolyte supplier 220, the indicator 230, the controller 240, and the electrode contact part 260 of the ancillary device 200 described with reference to FIGS. 4 and 5.

That is, the electrical stimulation device 400 of FIGS. 8 and 9 has a form obtained by combining the electrical stimulation device 100 of FIG. 1 and the ancillary device 200 for an electrical stimulation device described with reference to FIGS. 4 and 5.

It will be understood by those skilled in the art to which the inventive concept pertains that a form (not illustrated) obtained by combining the electrical stimulation device 100 of FIG. 1 and the ancillary device 300 for an electrical stimulation device described with reference to FIG. 7 may be provided.

Although the embodiments of the electrical stimulation devices 100 that apply an electrical stimulus to the head of the user have been described in the specification, the technical features of the inventive concept also may be applied to the electrical stimulation device for applying an electrical stimulus to another body portion of the user in addition to the head of the user in substantially the same manner.

The method described in relation to the embodiments of the inventive concept may be implemented by a software module performed by a processor. The software module may reside in a random access memory (RAM), an ROM, an EPROM, an EEPROM, a flash memory, a register, a hard disk, a detachable disk, a CD-ROM, or a computer readable recording medium of an arbitrary form that is known in the technical field to which the inventive concept pertains.

The inventive concept has the following effects.

First, because an electrode of the electrical stimulation device is neutralized by supplying a reverse current to the electrode, the pH index of the patch layer can be maintained in a safety range so that skin of the head of the user, which contacts the patch layer, can be prevented from being burned.

Second, because an electrolyte is supplied to an electrode of the electrical stimulation device, it helps a reverse reaction of a water splitting reaction by a reverse current supplied to the electrode and the concentration of the electrolyte of the patch layers can be maintained within a specific range so that an electricity transfer performance of the electrode can be maintained and the life span of the product can be extended.

Although the exemplary embodiments of the inventive concept have been described with reference to the accompanying drawings, it will be understood by those skilled in the art to which the inventive concept pertains that the inventive concept can be carried out in other detailed forms without changing the technical spirits and essential features thereof. Therefore, the above-described embodiments are exemplary in all aspects, and should be construed not to be restrictive.

What is claimed is:

1. An ancillary device for an electrical stimulation device comprising at least one electrode adapted to contact a head of a user to apply a current to the head of the user, the ancillary device being able to be applied to the electrical stimulation device, the ancillary device comprising:
   a reverse current supplier adapted to contact the at least one electrode of the electrical stimulation device;
   a controller that controls the reverse current supplier such that a reverse current is supplied to the at least one electrode to neutralize the at least one electrode; and
   a pH measurer that measures a pH index of the at least one electrode,
   wherein the controller controls the reverse current supplier such that the reverse current is supplied to the at least one electrode when the pH index of the at least one electrode, which is measured by the pH measurer, exceeds a reference pH index range.

2. The ancillary device of claim 1, further comprising:
   an indicator that indicates an operational state of the reverse current supplier.

3. An ancillary device for an electrical stimulation device comprising at least one electrode adapted to contact a head of a user to apply a current to the head of the user, the ancillary device being able to be applied to the electrical stimulation device, the ancillary device comprising:
   a reverse current supplier adapted to contact the at least one electrode of the electrical stimulation device;
   a controller that controls the reverse current supplier such that a reverse current is supplied to the at least one electrode to neutralize the at least one electrode;
   an electrolyte supplier adapted to contact the at least one electrode; and
   a concentration measurer that measures a concentration of an electrolyte of the at least one electrode,
   wherein the controller controls the electrolyte supplier such that the electrolyte is supplied to the at least one electrode when the concentration of the electrolyte of the at least one electrode, which is measured by the concentration measurer, is lower than a reference concentration.

4. The ancillary device of claim 3, further comprising:
   an indicator that indicates an operational state of the reverse current supplier or the electrolyte supplier.

5. An electrical stimulation device comprising:
   at least one electrode adapted to contact a head of a user to apply a current to the head of the user;
   a reverse current supplier that contacts the at least one electrode;
   a controller that controls the reverse current supplier such that a reverse current is supplied to the at least one electrode to neutralize the at least one electrode; and
   a pH measurer that measures a pH index of the at least one electrode,
   wherein the controller controls the reverse current supplier such that the reverse current is supplied to the at least one electrode when the pH index of the at least one electrode, which is measured by the pH measurer, exceeds a reference pH index range.

6. The electrical stimulation device of claim 5, further comprising:
   an indicator that indicates an operational state of the reverse current supplier.

7. An electrical stimulation device comprising:
   at least one electrode adapted to contact a head of a user to apply a current to the head of the user;
   a reverse current supplier that contacts the at least one electrode;
   a controller that controls the reverse current supplier such that a reverse current is supplied to the at least one electrode to neutralize the at least one electrode;
   an electrolyte supplier that contacts the at least one electrode; and
   a concentration measurer that measures a concentration of an electrolyte of the at least one electrode,
   wherein the controller controls the electrolyte supplier such that the electrolyte is supplied to the at least one electrode when the concentration of the electrolyte of the at least one electrode, which is measured by the concentration measurer, is lower than a reference concentration.

8. The electrical stimulation device of claim 7, further comprising:
   an indicator that indicates an operational state of the reverse current supplier or the electrolyte supplier.

* * * * *